United States Patent

Kawai et al.

[11] Patent Number: 6,071,504
[45] Date of Patent: Jun. 6, 2000

[54] HAIR TREATMENT COMPOSITION COMPRISING ALKALIZING AGENT

[75] Inventors: Tetsuya Kawai; Masahiko Ogawa; Naohisa Kure; Kenichi Matsunaga; Shinobu Nagase, all of Tokyo, Japan

[73] Assignee: Kao Corporation, Tokyo, Japan

[21] Appl. No.: 09/112,056

[22] Filed: Jul. 9, 1998

[30] Foreign Application Priority Data

Jul. 9, 1997 [JP] Japan ..................................... 9-183634
Dec. 22, 1997 [JP] Japan ..................................... 9-352956

[51] Int. Cl.$^7$ ................................ A61K 7/06; A61K 7/13
[52] U.S. Cl. ........................ 424/70.12; 424/70.1; 424/62; 424/401; 132/202; 132/208
[58] Field of Search ................................ 424/70.12, 70.1, 424/62, 401; 132/202, 208

[56] References Cited

U.S. PATENT DOCUMENTS 4,246,285   1/1981   Van Duzee .
4,710,314  12/1987   Madrange et al. .

FOREIGN PATENT DOCUMENTS 2 270 938  12/1995  France .
44 25 096   1/1995  Germany .
58-35106    1/1983  Japan .
10-25230    1/1998  Japan .
1 384 768   2/1975  United Kingdom .

*Primary Examiner*—Thurman K Page
*Assistant Examiner*—Brian K. Seidleck
*Attorney, Agent, or Firm*—Oblon, Spivak, McClelland, Maier & Neustadt, P.C.

[57] ABSTRACT

The invention relates to a hair treatment composition comprising (a) a guanidium salt, (b) an alkalizing agent other than the guanidium salt and (c) a silicone. The use of the hair treatment composition permits brightening the color tone of the hair or dyeing the hair in good shades from a bright shade to a deep shade. The composition scarcely damages the hair, gives off little irritating odor and has low irritativeness to the scalp.

4 Claims, No Drawings

HAIR TREATMENT COMPOSITION COMPRISING ALKALIZING AGENT

BACKGROUND OF THE INVENTION

1. Field of the Invention

The present invention relates to a hair treatment composition which can brighten the color tone of the hair or dye the hair in good shades from a bright shade to a deep shade for a short period of time, scarcely damages the hair, gives off little irritating odor and has low irritativeness to the scalp.

2. Description of the Background Art

In an oxidative hair-bleaching composition or hair dye composition, an alkalizing agent and an oxidizing agent are incorporated in a first-package formulation and a second-package formulation, respectively. The alkalizing agent is incorporated for the purpose of enhancing a bleaching or hair-dyeing effect and expediting oxidative decomposition of melanin granule in the hair to attain a light tone.

In order to bleach or dye the hair in a color tone lighter than its natural tone, a hair treatment used must have sufficient hair-bleaching ability. However, the hair-bleaching ability generally depends on the amount of an alkali, so that a sufficient amount of the alkali is required when the hair treatment is used for such purpose.

In general, ammonia has heretofore been used as an alkalizing agent. However, ammonia gives off a strong irritating odor and hence has a great defect that it gives users a considerable unpleasant feeling upon its use in bleaching or dyeing of hair.

Therefore, it has been attempted to use an organic amine, which gives off an odor to a lesser extent, in place of ammonia (Japanese Patent Application Laid-Open Nos. 106413/1974, 213220/1989, 246827/1993, etc.) However, the organic amine has insufficient bleachability and hence fails to bleach or dye the hair in a bright shade. In addition, the organic amine involves a problem that since it tends to remain on the scalp to a great extent, it gives users a feeling of physical disorder and irritates the scalp when used in a great amount.

SUMMARY OF THE INVENTION

Accordingly, it is an object of the present invention to provide a hair treatment composition which has sufficient bleachability, thus can brighten the color tone of the hair or dye the hair in a good shade, scarcely damages the hair, gives off little irritating odor, and has low irritativeness to the scalp.

In view of the foregoing circumstances, the present inventors have carried out an extensive investigation. As a result, it has been found that when a guanidium salt, an alkalizing agent and a silicone are used in combination, a hair treatment composition, which can brighten the color tone of the hair or dye the hair in good shades from a bright shade to a deep shade for a short period of time, scarcely damages the hair, gives off little irritating odor and has low irritativeness to the scalp, is obtained, thus leading to completion of the present invention.

According to the present invention, there is thus provided a hair treatment composition comprising (a) a guanidium salt, (b) an alkalizing agent other than the guanidium salt and (c) a silicone.

DETAILED DESCRIPTION OF THE PREFERRED EMBODIMENTS

Examples of the guanidium salt, which is the component (a) of the composition according to the present invention, include guanidine hydrochloride, guanidine sulfate, guanidine nitrate, guanidine carbonate, guanidine hydrogencarbonate, guanidine phosphate, guanidine thiocyanate, guanidine borate, and the guanidine salts of organic acids, such as guanidine sulfamate, guanidine acetate, guanidine monoethyl oxalate, guanidine benzenesulfonate and guanidine alizarin disulfonate. Guanidine carbonate and guanidine hydrogencarbonate are particularly preferred.

These salts may be used either singly or in any combination thereof. The component (a) is preferably incorporated in a proportion of 0.1 to 10 wt. %, particularly 0.5 to 3 wt. % based on the total weight of the composition. The component (a) used within this range permits the attainment of a sufficient dyeing effect: because when an oxidizing agent is mixed therewith, the activating reaction of the oxidizing agent is not expedited in excess, and a dye intermediate does not produce a dye before it penetrates into the hair, and reduction in emission of an irritating odor and irritation of the skin.

No particular limitation is imposed on the alkalizing agent of the component (b) so far as it is an alkalizing agent other than the guanidium salt. However, ammonia and/or alkanolamines are preferred. Examples of the alkanolamines include ethanolamine, diethanolamine, triethanolamine, monopropanolamine, isopropanolamine, dipropanolamine, tripropanolamine, 2-amino-2-methyl-1,3-propanediol and 2-amino-2-hydroxymethyl-1,3-propanediol. These alkalizing agents may be used either singly or in any combination thereof.

When ammonia among these alkalizing agents is incorporated, it is preferably incorporated in a proportion of 0.01 to 3 wt. %, particularly 0.1 to 1 wt. % based on the total weight of the composition, in that a sufficient effect can be brought about, and besides no irritating odor is given off and no unpleasant feeling is produced during treatment of the hair. When an alkanolamine is incorporated, it is preferably incorporated in a proportion of 0.1 to 10 wt. %, particularly 0.5 to 3 wt. % based on the total weight of the composition, in that a sufficient effect can be brought about, and besides no feeling of physical disorder to the scalp is produced.

Incidentally, the total amount of the alkalizing agent (b) to be incorporated is preferably 0.01 to 20 wt. %, particularly 0.1 to 7 wt. % based on the total weight of the composition.

Examples of the silicone of the component (c) include polyether-modified silicone, amino-modified silicone, long chain alkyl-modified silicone, alkoxy-modified silicone, Bunte salt-modified silicone, oxazoline-modified silicone elastomer, dimethyl polysiloxane and methylphenyl polysiloxane. Of these, polyether-modified silicone and amino-modified silicone are preferred. Polyether-modified silicone includes those represented by the following formulae (1) to (4):

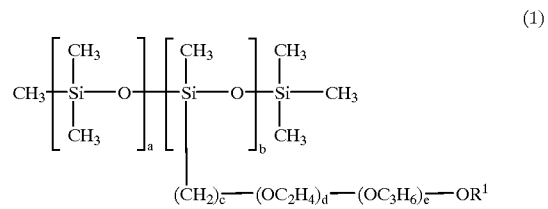

-continued

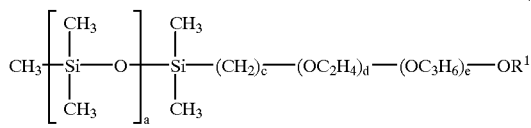
(2)

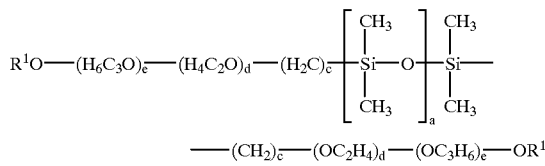
(3)

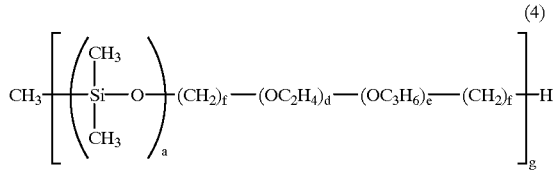
(4)

wherein $R^1$ is a hydrogen atom or a hydrocarbon group having 1 to 10 carbon atom, a is a number of 15 or greater, b is a number of 1 or greater, c is a number of 1 to 6, d is a number of 1 to 300, e is a number of 0 to 300, f is a number of 0 to 6, and g is a number of 2 to 500.

The hydrocarbon group represented by $R^1$ in the formulae is preferably a linear or branched hydrocarbon group having 1 to 8 carbon atoms, with a methyl group being particularly preferred. $R^1$ is preferably a hydrogen atom. a is preferably a number of 20 to 500, b is preferably a number of 1 to 100, c is preferably a number of 2 to 4, d is preferably a number of 2 to 50, e is preferably a number of 0 to 50, f is preferably a number of 2 to 4, and g is preferably a number of 2 to 50.

When a in the formulae is smaller than 15, the resulting hair treatment composition cannot give users an pleasant finish feeling. It is hence not preferable to use such a polyether-modified silicone.

Of the polyether-modified silicones represented by the formulae (1) to (4), those represented by the formula (1) are particularly preferred.

The amino-modified silicone includes those represented by the formula (5):

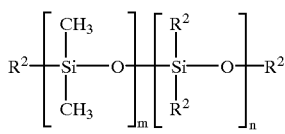
(5)

wherein radicals $R^2$ may be the same or different frown each other and are individually a hydrogen atom, or a hydroxyl, methyl or methoxy group, $R^3$ is —$(CH_2)_o$—$(OC_2H_4)_p$—$(OC_3H_6)_q$—$(NHC_2H_4)N(R^4)_2$ or —$(CH_2)_o$—$(OC_2H_4)_p$—$(OC_3H_6)_q$—$(NHC_2H_4)N^+(R^4)_3 \cdot Z^-$ (in which radicals $R^4$ may be the same or different from each other and are individually a hydrogen atom, or a hydrocarbon group having 1 to 6 carbon atoms, Z is a halogen ion or organic anion, o is a number of 1 to 6, and p and q are individually a number of 0 to 6), m is a number of 3 to 300, and n is a number of 1 to 30.

In the formula (5), $R^2$ is preferably a hydroxyl or methyl group, $R^3$ is preferably —$(CH_2)_3$—$NHC_2H_4NH_2$, m is preferably a number of 3 to 300, and n is preferably a number of 1 to 20.

These silicones (c) may be used either singly or in any combination thereof and are preferably incorporated in an amount of 0.01 to 10 wt. %, particularly 0.1 to 6 wt. % based on the total weight of the composition.

In the composition according to the present invention, it is preferable from the viewpoint of bleaching and dyeing effects that (d) an aromatic alcohol represented by the following general formula (A):

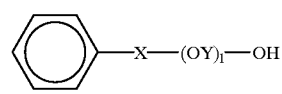
(A)

wherein l is 0 or 1, and X is a linear or branched alkylene, alkenylene or alkylenoxy group having 2 to 6 carbon atoms when l is 0, with the proviso that the oxygen atom of the alkylenoxy group is bonded to the benzene ring, or X and Y are individually a linear or branched alkylene group having 1 to 6 carbon atom when l is 1, be incorporated.

When l in the formula (A) is 0, X is preferably a linear or branched alkylene or alkylenoxy group having 2 to 4 carbon atoms. When l is 1 on the other hand, X and Y are preferably a methylene group and a linear alkylene group having 2 to 6 carbon atoms, respectively.

Specific examples of the aromatic alcohol of the component (d) include phenylethyl alcohol, phenoxyethanol, phenoxyisopropanol, α-methylbenzyl alcohol, α,α-dimethylbenzyl alcohol, α-propylberzyl alcohol, 2-benzyloxyethanol and 3-benzyloxybutanol, with pherylethyl alcohol and 2-benzyloxyethanol being particularly preferred.

The aromatic alcohols of the component (d) may be used either singly of in any combination thereof and are preferably incorporated in a proportion of 0.1 to 30 wt. % based on the total weight of the composition. It is more preferable that they be incorporated in a proportion of 1 to 10 wt. %, particularly 3 to 7 wt. % based on the total weight of the composition because the composition can be provided as a composition which has sufficient bleaching and dyeing ability and gives users no feeling of physical disorder to the scalp.

In the composition according to the present invention, an oxidative dye intermediate may be incorporated as a component (e), so that the composition can be provided as a composition that can dye the hair in a good shade. As such oxidative dye intermediates, there may be used known developing substances and coupling substances commonly used in the classical oxidative hair dye compositions.

Of these, examples of the developing substances include p-phenylenediamines having one or few —$NH_2$, —NHR or —$NR_2$ groups (in which R is an alkyl or hydroxyalkyl group having 1 to 4 carbon atoms), such as p-phenylendinine, p-toluenediamine, N-methyl-p-phenylenediamine, N,N-dimethyl-p-phenylenediamine, N,N-diethyl-2-methyl-p-phenylenediamine, N-ethyl-N-(hydroxyethyl)-p-phenylenediamine, chloro-p-phenylenediamine, 2-(2'-hydroxyethylamino)-5-aminotoluene, N,N-bis-(2-hydroxyethyl)-p-phenylenediamine, methoxy-p-phenylenediamine, 2,6-dichloro-p-phenylenediamine, 2-chloro-6-bromo-p-phenylenediamine, 2-chloro-6-methyl-p-phenylenediamine, 6-methoxy-3-methyl-p-phenylenediamine, 2,5-diaminoanisole, N-(2-hydroxypropyl)-p-phenylenediamine, N-2-methoxyethyl-p-phenylenediamine and 1-β-hydroxyethyl-2,5-diaminobenzene; 2,5-diaminopyridine derivatives;

p-aminophenols such as p-aminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, 2,5-dimethyl-4-aminophenol, 2,4-diaminophenol and 5-aminosalicylic acid; o-aminophenols; and o-phenylenediamines.

When a p-aminophenol and/or an o-aminophenol among these developing substances is incorporated, a light color tone of a system from yellow to reddish brown can be developed. Further, when this developing substance is used, the dyeability of the resulting composition is enhanced, and the hair is dyed in a bright shade so long as a guanidine derivative is additionally used in combination with ammonia.

Examples of the coupling agents include α-naphthol, o-cresol, m-cresol, 2,6-dimethylphenol, 2,5-dimethylphenol, 3,4-dimethylphenol, 3,5-dimethylphenol, benzcatechin, pyrogallol, 1,5-dihydroxynaphthalene, 1,7-dihydroxynaphthalene, 5-amino-2-methylphenol, 5-(2-hydroxyethylamino)-2-methylphenol, 5-(2'-hydroxyethylamino)- 4-methoxy-2-methylphenol, hydroquinone, 2,4-diaminoanisole, m-toluylenediamine, 4-aminophenol, resorcin, resorcin monomethyl ether, 2-amino-4-hydroxyethylaminoanisole, m-phenylenediamine, 1-phenyl-3-methyl-5-pyrazolone, 1-phenyl-3-amino-5-pyrazolone, 1-phenyl-3,5-diketopyrazolidine, 1-methyl-7-dimethylamino-4-hydroxy-2-quinolone, m-aminophenol, 4-chlororesorcin, 2-methylresorcin, 2,4-diaminophenoxyethanol, 2,6-diaminopyridine, 2-amino-3-hydroxypyridine, 3,5-diaminotrifluoromethylbenzene, 2,4-diaminofluorobenzene, 3,5-diaminofluorobenzene, 2,4-diamino-6-hydroxypyrimidine, 2,4,6-triaminopyrimidine, 2-amino-4,6-dihydroxypyrimidine, 4-amino-2,6-dihydroxypyrimidine, 4,6-diamino-2-hydroxypyrimidine.

These developing substances and coupling substances may be used either singly or in any combination thereof. No particular limitation is imposed on the amounts of these substances to be incorporated. However, it is preferable to incorporate them in a proportion of 0.01 to 20 wt. %, particularly 0.5 to 10 wt. %, each, based on the total weight of the composition.

It is also permissible to additionally change the color shade of the hair by using a composition obtained by further incorporating a direct dye into the hair treatment composition according to the present invention. Such direct dyes include those described in the Dye Raw Material Standard issued by Japan Hair Color Industry Association. Of these, nitrophenylenediamine, nitroaminophenol and anthraquinone dyes are particularly preferred.

When these direct dyes are incorporated in the hair treatment composition according to the present invention, the total amount thereof is preferably in a proportion of 0.001 to 20 wt. %, particularly 0.01 to 10 wt. % based on the total weight of the composition.

When the oxidative dye intermediate is incorporated in the hair treatment composition according to the present invention, oxidative coupling is caused even by oxygen in the air, whereby the hair or the like is dyed. It is however preferable to cause oxidative coupling by adding an oxidizing agent to the composition. Examples of particularly preferred oxidizing agents include hydrogen peroxide; products with hydrogen peroxide added to urea, melamine or sodium borate; and mixtures of such a hydrogen peroxide adduct with potassium peroxodisulfate.

Besides the above components, other optional ingredients commonly used in the field of cosmetic compositions may be suitably added to the hair treatment compositions according to the present invention so far as no detrimental influence is thereby imposed on the effects of the present invention. Examples of such optional ingredients include viscosity and gel-strength adjustors, such as natural or synthetic polymers such as gum arabic, locust bean gum, sodium alginate, xanthan gum, cellulose derivatives and crosslinked polyacrylic acid, and fatty acids; oils and fats such as glycerides of abocado oil, jojoba oil, macadamia nut oil and olive oil; waxes such as beeswax and lanolin; hydrocarbons such as liquid paraffin, solid paraffin, isoparaffin and squalane; polyhydric alcohols such as propylene glycol, glycerol, 1,3-butylene glycol, polyglycerol and sorbitol; esters such as isopropyl myristate and octyldodecyl myristate; amides such as oleic diethanolamide and lauric diethanolamide; cationic surfactants such as stearyltrimethylammonium chloride and distearyldimethylammonium chloride; anionic surfactants such as polyoxyethylene lauryl ether sulfate and polyoxyethylene lauryl sulfosuccinate; amphoteric surfactants such as laurylhydroxysulfobetaine and lauryldimethylcarbobetaine; nonionic surfactants such as polyoxyethylene alkyl ether and polyoxyethylene alkyl phenyl ether; nonionic polymers such as polyvinyl pyrrolidone and copolymers of vinylpyrrolidone and vinyl acetate; anionic polymers such as copolymers of acrylic acid and/or methacrylic acid and an alkyl (meth)acrylate; amphoteric polymers such as copolymers of N-methacryloyl-ethyl-N,N-dimethylammonium-α-N-methylcarboxybetaine and butyl methacrylate; protein derivatives and amino acids such as hydrolyzates of collagen and keratin; antiseptics such as parabens; chelating agents such as sodium ethylenediaminetetraacetate; stabilizers such as phenacetin and 8-hydroxyquinoline; antioxidants such as thioglycolic acid, sulfites and ascorbic acid; and besides plant extracts, crude drug extracts, vitamins, coloring matter, perfume bases, pigments and ultraviolet absorbents.

The hair treatment compositions according to the present invention can be prepared in accordance with a method known per se in the art, and no particular limitation is imposed on the preparation forms thereof. They may be formulated in the forms of, for example, transparent solutions, emulsions, cream, gel, paste, mousse and the like.

Incidentally, the hair treatment compositions according to the present invention are preferably kept at pH 8 to 12, particularly 9 to 11. Any pH lower than 8 results in a failure to sufficiently achieve the object of the present invention. On the other hand, any pH higher than 12 results in a composition which has strong irritativeness to the scalp and cannot practically used. The adjustment of the pH may be suitably conducted with a buffer such as ammonium chloride, ammonium carbonate, ammonium hydrogencarbonate, ammonium phosphate, ammonium nitrate or ammonium sulfate.

The hair treatment composition according to the present invention is mixed with an oxidizing agent composition containing hydrogen peroxide or the like, which is a second-package formulation, at a weight ratio of 1:1 to 1:3 upon its use.

In order to bleach or dye the hair with the hair treatment composition according to the present invention, it is only necessary to apply, for example, a liquid mixture prepared by adding the oxidizing agent composition to the hair treatment composition according to the present invention to the hair at a temperature of 15 to 40° C., rinse out the hair after the operating time of about 1 to 50 minutes, preferably about 10 to 30 minutes and dry the hair.

The present invention will hereinafter be described in more detail by the following examples. However, the present invention is not limited to these examples.

EXAMPLES 1 TO 3 AND COMPARATIVE EXAMPLES 1 TO 5

First-package formulations (invention products and comparative products) of their corresponding compositions shown in Table 1 and a second-package formulation of a composition shown in Table 2 were separately prepared in accordance with a method known per se in the art. All equal amount (by weight) of the second-package formulation was added to each of the first-package formulations.

These mixtures were separately applied to whites-hair tresses, and the tresses were left to stand for 15 minutes at 30° C. and then rinsed out, shampooed and dried. These mixtures were then evaluated as to dyeability to these tresses and damage to the hair in accordance with the following respective methods.

Besides, these mixtures were separately applied to black-hair tresses, and the tresses were left to stand for 15 minutes at 30° C. and then rinsed out, shampooed and dried. These mixtures were then evaluated as to brightening ability to the tresses in accordance with the following method.

Further, these mixture were evaluated as to irritating odor and irritativeness to the scalp in accordance with the respective following methods.

These results are shown collectively in Table 1.

<Evaluation methods>

(1) Dyeability:

The white-hair tresses dyed were visually observed to evaluate the mixtures as to dyeability in accordance with the following standard:

○: Evenly and fast dyed;

Δ: Somewhat uneven, and not very dyed;

X: Uneven, and scarcely dyed.

(2) Damage to the Hair:

The surfaces of the black-hair and white-hair tresses dyed were observed through an electron microscope (3,000 magnifications) to determine the degree of damage to cuticula pili, thereby evaluating the mixtures as to the damage to the hair in accordance with the following standard:

○: Damage were scarcely observed;

Δ: Damage such as protuberance, rhagades or abrasion was somewhat observed on cuticula pili;

X: Damage such as protuberance, rhagades or abrasion was considerably observed on cuticula pili.

(3) Brightening Ability:

The black-hair tresses dyed were visually observed to evaluate the mixtures as to brightening ability in accordance with the following standard:

○: Dyed in a natural and bright shade of brown;

Δ: Dyed in a somewhat dark shade of brown;

X: Dyed in a dark shade of blackish brown.

(4) Irritating Odor:

Each of the first-package formulations was mixed with the second-package formulation by hand, and the resulting mixture was evaluated as to odor in accordance with the following standard:

○: Scarcely smelled of an irritating odor;

Δ: Slightly smelled of an irritating odor;

X: Strongly smelled of an irritating odor.

(5) Irritativeness to the Scalp:

A mixture of each of the first-package formulations and the second-package formulation was applied to the scalp, and the mixture was evaluated as to irritativeness to the scalp in accordance with the following standard:

○: Scarcely felt an irritation;

Δ: Slightly felt an irritation;

X: Strongly felt an irritation.

TABLE 1

(wt. %)

| Component | Example 1 | Example 2 | Example 3 | Comparative Example 1 | Comparative Example 2 | Comparative Example 3 | Comparative Example 4 | Comparative Example 5 |
|---|---|---|---|---|---|---|---|---|
| Aqueous ammonia (28%)*1 | 0.8 | 0.3 | 1.5 | 3.2 | — | — | 0.8 | 0.8 |
| Monoethanolamine | 2.0 | 4.0 | — | — | 12.0 | — | 2.0 | 2.0 |
| Guanidine carbonate | 1.5 | 1.5 | 1.5 | — | — | 12.0 | — | 1.5 |
| Amino-modified silicone*2 | 3.0 | 3.0 | 3.0 | 3.0 | 3.0 | 3.0 | 3.0 | — |
| Cetanol | 8.5 | 8.5 | 8.5 | 8.5 | 8.5 | 8.5 | 8.5 | 8.5 |
| Toluene-2,5-diamine | 1.0 | 1.0 | 1.0 | 1.0 | 1.0 | 1.0 | 1.0 | 1.0 |
| Resorcin | 0.6 | 0.6 | 0.6 | 0.6 | 0.6 | 0.6 | 0.6 | 0.6 |
| m-Aminophenol | 0.4 | 0.4 | 0.4 | 0.4 | 0.4 | 0.4 | 0.4 | 0.4 |
| Polyoxyethylene (40) cetyl ether | 3.0 | 3.0 | 3.0 | 3.0 | 3.0 | 3.0 | 3.0 | 3.0 |
| Polyoxyethylene (2) cetyl ether | 3.5 | 3.5 | 3.5 | 3.5 | 3.5 | 3.5 | 3.5 | 3.5 |
| Stearyltrimethylammonium chloride | 2.0 | 2.0 | 2.0 | 2.0 | 2.0 | 2.0 | 2.0 | 2.0 |
| Liquid paraffin | 0.5 | 0.5 | 0.5 | 0.5 | 0.5 | 0.5 | 0.5 | 0.5 |
| Sodium sulfite | 0.5 | 0.5 | 0.5 | 0.5 | 0.5 | 0.5 | 0.5 | 0.5 |
| Ascorbic acid | 0.5 | 0.5 | 0.5 | 0.5 | 0.5 | 0.5 | 0.5 | 0.5 |
| Tetrasodium edetate | 0.1 | 0.1 | 0.1 | 0.1 | 0.1 | 0.1 | 0.1 | 0.1 |
| Perfume base | 0.4 | 0.5 | 0.5 | 0.5 | 0.5 | 0.5 | 0.5 | 0.5 |
| Ammonium chloride | Amount sufficient to adjust pH to 10.0 | | | | | | | |
| Water | Balance | | | | | | | |
| Evaluated items Dyeability | ○ | ○ | ○ | ○ | X | X | Δ | ○ |
| Damage to the hair | ○ | ○ | ○ | X | X | X | ○ | X |
| Brightening ability | ○ | ○ | ○ | Δ | X | X | X | ○ |
| Irritating odor | ○ | ○ | ○ | X | ○ | ○ | ○ | ○ |
| Irritativeness to the scalp | ○ | ○ | ○ | X | X | X | ○ | ○ |

*1The amount incorporated was expressed as the amount of NH$_3$.
*2SM8702C, trade name; product of Toray Dow Corning Silicone Co., Ltd.

TABLE 2

| Component | Amount incorporated (wt. %) |
|---|---|
| Hydrogen peroxide (35%) | 17.1 |
| Methylparaben | 0.1 |
| Phosphoric acid | Amount sufficient to adjust pH to 3.5 |
| Water | Balance |

EXAMPLE 4

A first-package formulation of a composition shown in Table 3 was prepared in accordance with a method known per se in the art, and an equal amount (by weight) of the second-package formulation of the composition shown in Table 2 was added to and mixed with the first-package formulation.

The mixture was applied to black-hair tresses and the tresses were left to stand for 15 minutes at 30° C. and then rinsed out, shampooed and dried. The mixture was then evaluated as to dyeability to these tresses, damage to the hair, brightening ability, irritating odor and irritativeness to the scalp in accordance with the same respective methods and standards as in Example 1.

As a result, the mixture was ranked as ○ in all the evaluated items.

TABLE 3

| Component | Amount incorporated (wt. %) |
| --- | --- |
| Aqueous ammonia (28%)*[1] | 0.8 |
| Monoethanolamine | 2.0 |
| Guanidine carbonate | 1.5 |
| Oleyl alcohol | 2.0 |
| Polyether-modified silicone*[2] | 1.0 |
| m-Aminophenol | 0.8 |
| o-Aminophenol | 1.0 |
| Oleic acid | 10.0 |
| Oleic diethanolamide | 8.0 |
| Polyoxyethylene (20) octyl dodecyl ether | 10.0 |
| Ethanol | 15.0 |
| Propylene glycol | 10.0 |
| 2-Benzyloxyethanol | 5.0 |
| Sodium sulfite | 0.5 |
| Ascorbic acid | 0.5 |
| Tetrasodium edetate | 0.1 |
| Perfume base | 0.4 |
| Ammonium chloride | Amount sufficient to adjust pH to 10.0 |
| Water | Balance |

*[1]The amount incorporated was expressed as the amount of $NH_3$.
*[2]KF10005, trade name; product of Shin-Etsu Chemical Co., Ltd.

EXAMPLE 5

First-package and second-package formulations of the following respective compositions were prepared in accordance with a method known per se in the art. A equiamount mixture of the first-package formulation and the second-package formulation could give the hair a bright shade. In addition, it neither damaged the hair nor irritated the scalp.

First-package Formulation:

| Component | (wt. %) |
| --- | --- |
| Guanidine carbonate | 2.0 |
| Aqueous ammonia (28%)*[1] | 1.0 |
| Monoethanolamine | 3.0 |
| Ethanol | 15.0 |
| Propylene glycol | 10.0 |
| Oleic acid | 3.0 |
| Oleic diethanolamide | 6.0 |
| Amino-modified silicone*[2] | 1.0 |
| Oleyl alcohol | 2.0 |
| Polyoxyethylene (20 E.O.) octyl dodecyl ether | 10.0 |
| Tetrasodium edetate | 0.1 |
| Ammonium chloride*[3] | q.s. |
| Purified water | Balance |
| Total | 100.0 |

*[1]The amount incorporated was expressed as the amount of $NH_3$.
*[2]SM8702C, trade name; product of Toray Dow Corning Silicone Co., Ltd.
*[3]Amount sufficient to adjust pH to 10.0.

Second-package Formulation:

| Component | (wt. %) |
| --- | --- |
| Cetanol | 2.0 |
| Sodium alkyl sulfate | 1.0 |
| Hydrogen peroxide | 6.0 |
| Phosphoric acid*[4] | q.s. |
| Purified water | Balance |
| Total | 100.0 |

*[4]Amount sufficient to adjust pH to 3.5.

As described above, the hair treatment compositions according to the present invention can brighten the color tone of the hair or dye the hair in good shades from a bright shade to a deep shade for a short period of time, scarcely damages the hair, give off little irritating odor and have low irritativeness to the scalp.

This application is based on Japanese Patent applications; No. 9-183634, filed Jul. 9, 1997 and No. 9-352956, filed Dec. 22, 1997, which are herein incorporated by reference.

What is claimed is:

1. A hair treatment composition comprising:

(a) 0.1 to 10 wt. % of a guanidium salt;

(b) 0.01 to 20 wt. % of an alkalizing agent selected from the group consisting of ammonia, an alkanolamine and a mixture thereof; and (c) 0.01 to 20 wt. % of an amino-modified silicone of the formula:

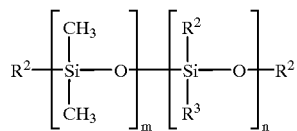

wherein $R^2$ may be the same or different from each other and are individually a hydrogen atom, or a hydroxyl, methyl or methoxy group, $R^3$ is $-(CH_2)_o-(OC_2H_4)_p-(OC_3H_6)_q-(NHC_2H_4N(R^4)_2$ or $-(CH_2)_o-(OC_2H_4)_p-(OC_3H_6)_q-(NHC_2H_4)N^+(R^4)_3 \cdot Z^-$, in which radicals $R^4$ may be the same or different from each ether and are individually a hydrogen atom, or a hydrocarbon group having 1 to 6 carbon atoms, Z is a halogen ion or organic anion, o is a number from 1 to 6, and p and q are individually a number of 0 to 6, m is a number of 3 to 300, and n is a number of 1 to 30.

2. The hair treatment composition according to claim 1, which further comprises (d) an aromatic alcohol represented by the following formula (A):

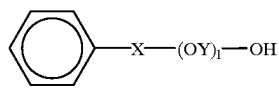

(A)

wherein l is 0 or 1, and X is a linear or branched alkylene, alkenylene or alkylenoxy group having 2 to 6 carbon atoms when l is 0, with the proviso that the oxygen atom of the alkylenoxy group is bonded to the benzene ring, or X and Y are individually a linear or branched alkylene group having 1 to 6 carbon atom when l is 1.

3. The hair treatment composition according to claim 1, which further comprises (e) an oxidative dye intermediate.

4. The hair treatment composition according to claim 1, which is mixed with an oxidizing agent upon its use.

* * * * *